(12) United States Patent
Gutelius et al.

(10) Patent No.: US 10,512,466 B2
(45) Date of Patent: Dec. 24, 2019

(54) ADAPTER ASSEMBLY FOR SURGICAL DEVICE

(71) Applicant: Covidien LP, Mansfield, CT (US)

(72) Inventors: Patrick N. Gutelius, Monroe, CT (US); Khalil R. Khouri, Key Biscayne, FL (US); Jeffrey P. Radziunas, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 474 days.

(21) Appl. No.: 15/297,178

(22) Filed: Oct. 19, 2016

(65) Prior Publication Data

US 2017/0128074 A1 May 11, 2017

Related U.S. Application Data

(60) Provisional application No. 62/251,300, filed on Nov. 5, 2015.

(51) Int. Cl.
*A61B 17/115* (2006.01)
*A61B 17/34* (2006.01)
*A61B 17/00* (2006.01)

(52) U.S. Cl.
CPC ...... *A61B 17/1155* (2013.01); *A61B 17/3496* (2013.01); *A61B 2017/0046* (2013.01); *A61B 2017/00323* (2013.01); *A61B 2017/00473* (2013.01); *A61B 2017/00486* (2013.01)

(58) Field of Classification Search
CPC .............. A61B 17/115; A61B 17/1155; A61B 2017/00323; A61B 2017/00327
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Jul. 13, 2017, issued in EP Application No. 16197375.

(Continued)

*Primary Examiner* — Stephen F. Gerrity
*Assistant Examiner* — Joshua G Kotis

(57) ABSTRACT

An adapter assembly for connecting an end effector to a surgical instrument includes first and second drive assemblies configured for converting rotational motion into linear motion, and an actuation assembly. The second drive assembly includes a pair of push/pull cables for longitudinally advancing and retracting a drive member.

19 Claims, 13 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,571,116 A * | 11/1996 | Bolanos ............ A61B 17/07207 227/175.3 |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,506 A | 2/1998 | Arabia, Jr. et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2003/0218047 A1* | 11/2003 | Sharma ............ A61B 17/07207 227/176.1 |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0288573 A1 | 11/2011 | Yates et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0197190 A1* | 8/2012 | Suon ................ A61B 17/2909 604/95.04 |
| 2012/0232339 A1 | 9/2012 | Csiky |
| 2012/0273548 A1 | 11/2012 | Ma et al. |
| 2012/0292367 A1* | 11/2012 | Morgan ............ A61B 17/072 227/175.1 |
| 2012/0310220 A1* | 12/2012 | Malkowski ............ A61B 17/29 606/1 |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |

(56) References Cited

U.S. PATENT DOCUMENTS

| | | |
|---|---|---|
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0005681 A1* | 1/2014 | Gee ............... A61B 17/320092 606/130 |
| 2014/0008413 A1 | 1/2014 | Williams |
| 2014/0012317 A1 | 1/2014 | Orban et al. |
| 2014/0025046 A1* | 1/2014 | Williams ......... A61B 17/07207 606/1 |
| 2014/0194893 A1* | 7/2014 | Jeong ..................... A61B 17/29 606/130 |
| 2015/0223818 A1 | 8/2015 | Racenet et al. |
| 2016/0316996 A1* | 11/2016 | Nakayama ........... A61B 1/0055 |
| 2017/0102055 A1* | 4/2017 | Gutelius ............ A61B 17/3476 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2823771 A1 | 1/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013-138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2004032763 A2 | 4/2004 |
| WO | 2008/107918 A1 | 9/2008 |
| WO | 2015139197 A1 | 9/2015 |

OTHER PUBLICATIONS

European Search Report dated Mar. 14, 2017, issued in EP Application No. 16197375.
Extended European Search Report from Appl. No. 14181908.6 dated May 26, 2015.
European Examination Report from Appl. No. 14181908.6 dated May 3, 2016.

* cited by examiner

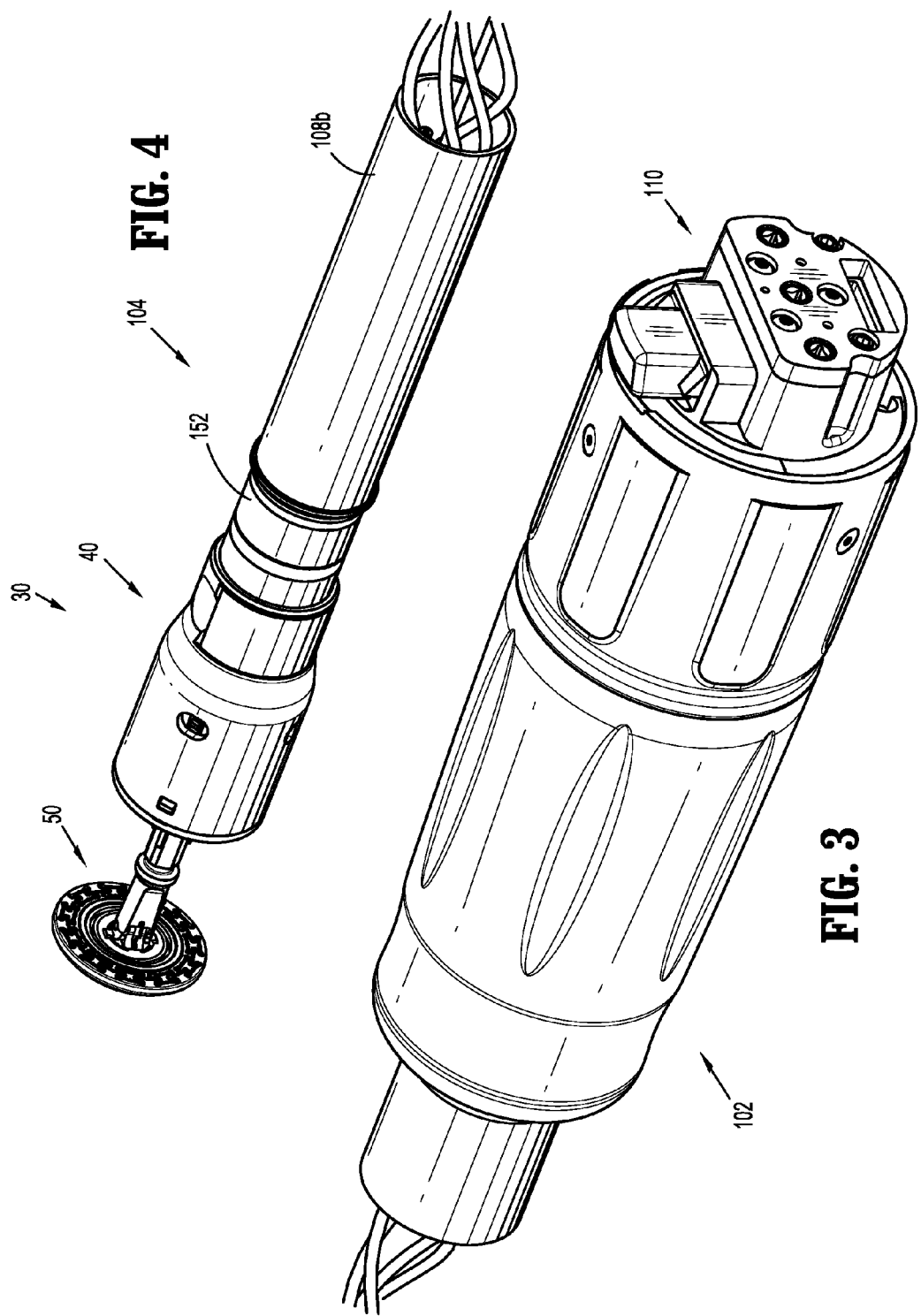

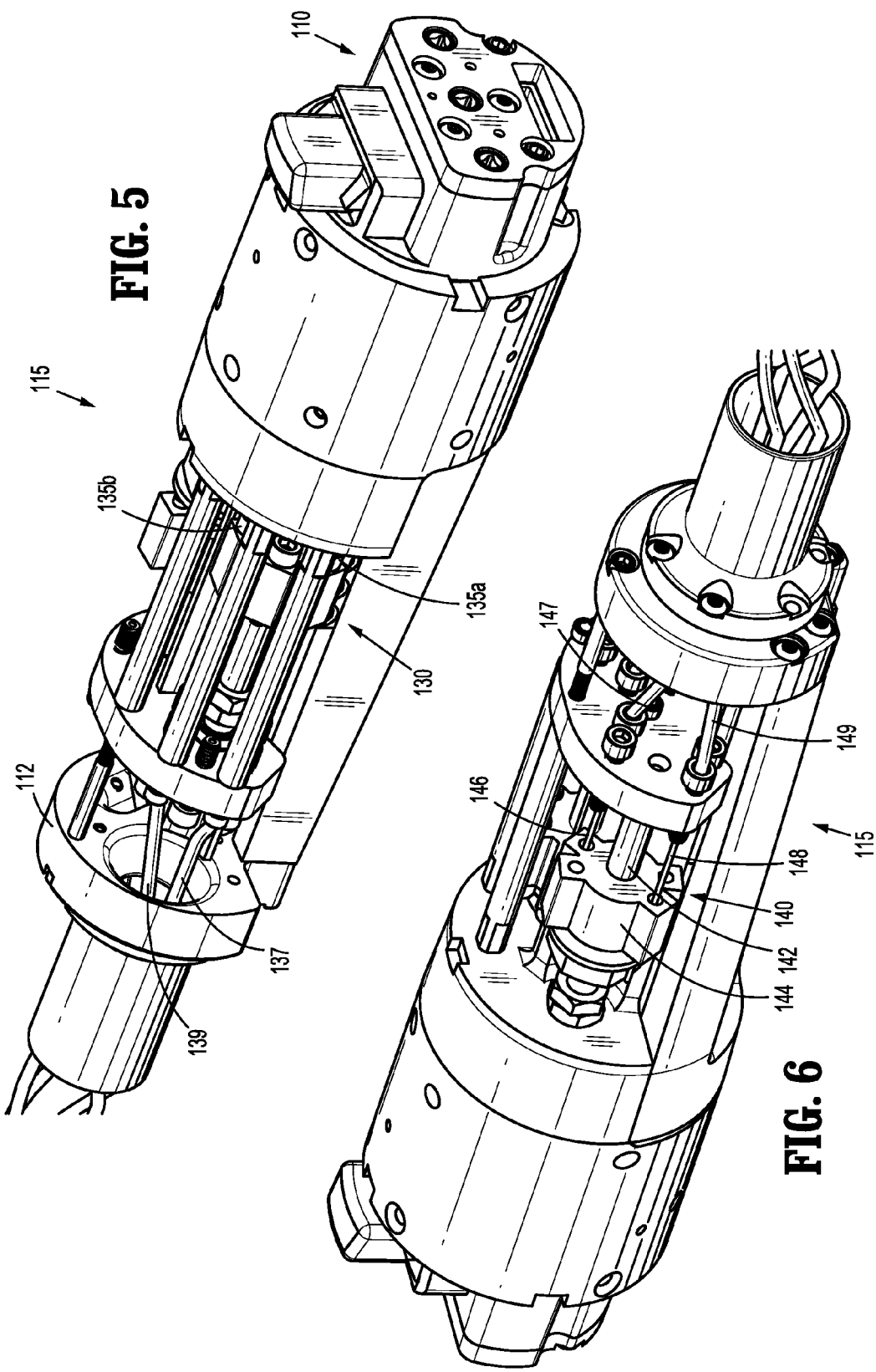

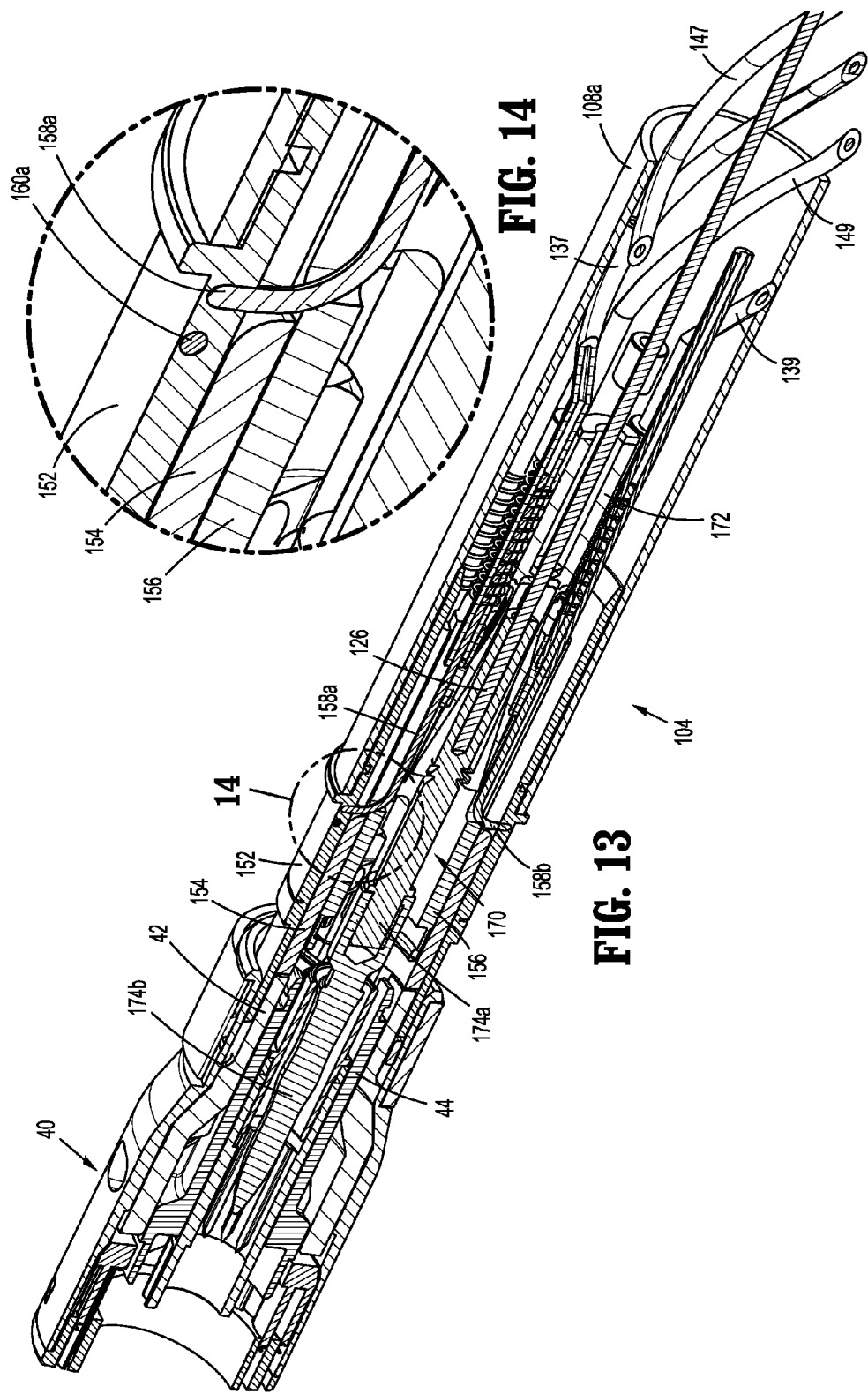

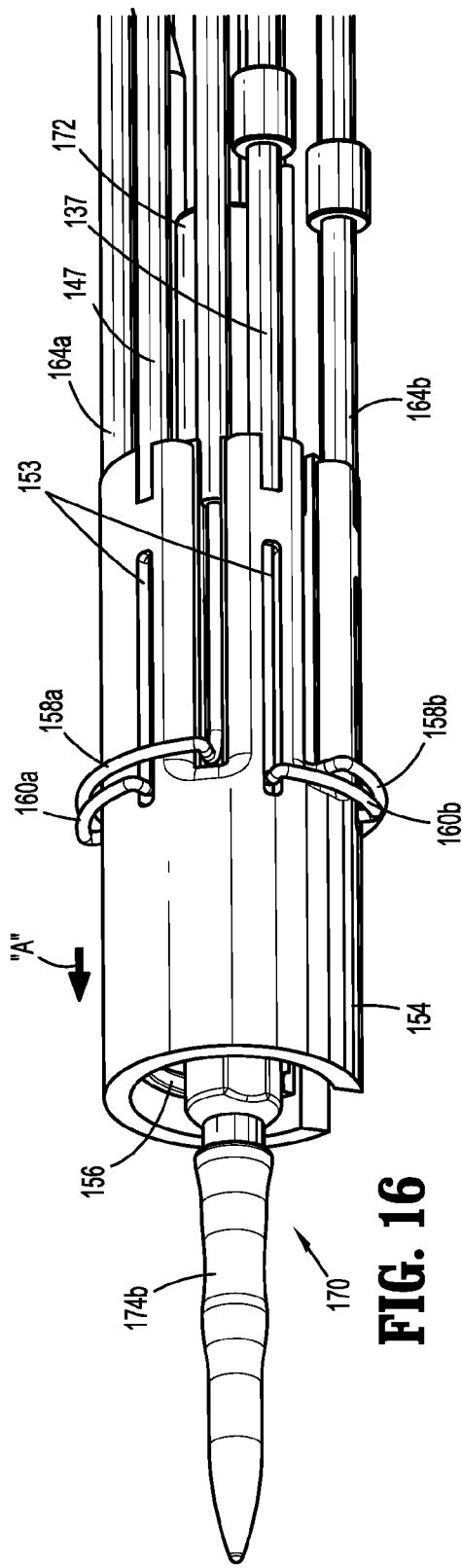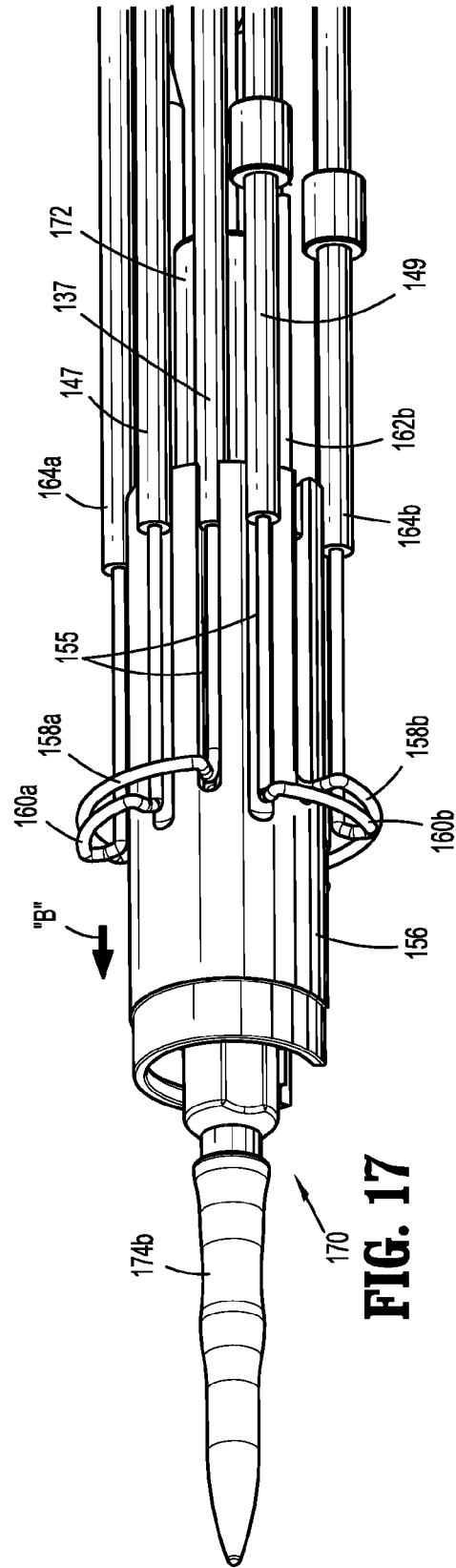

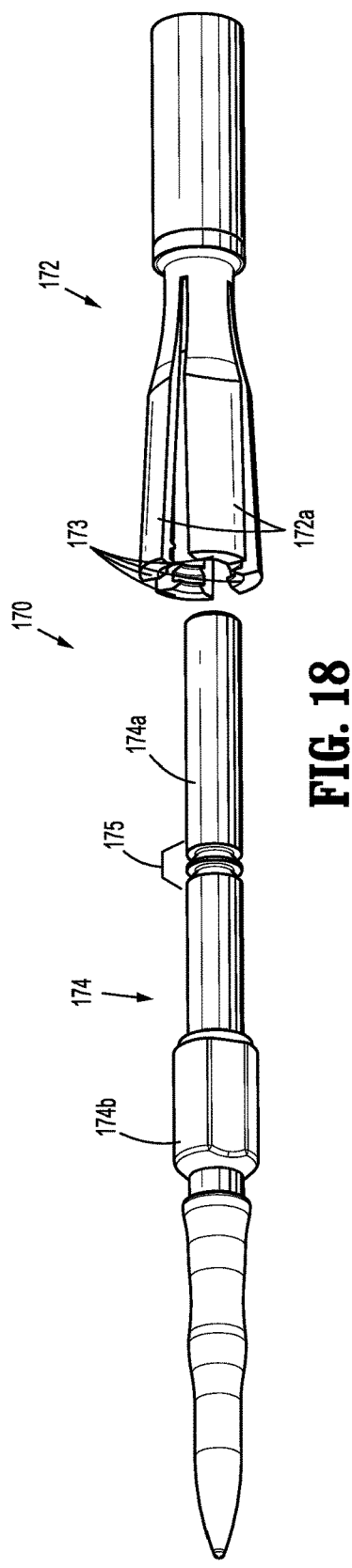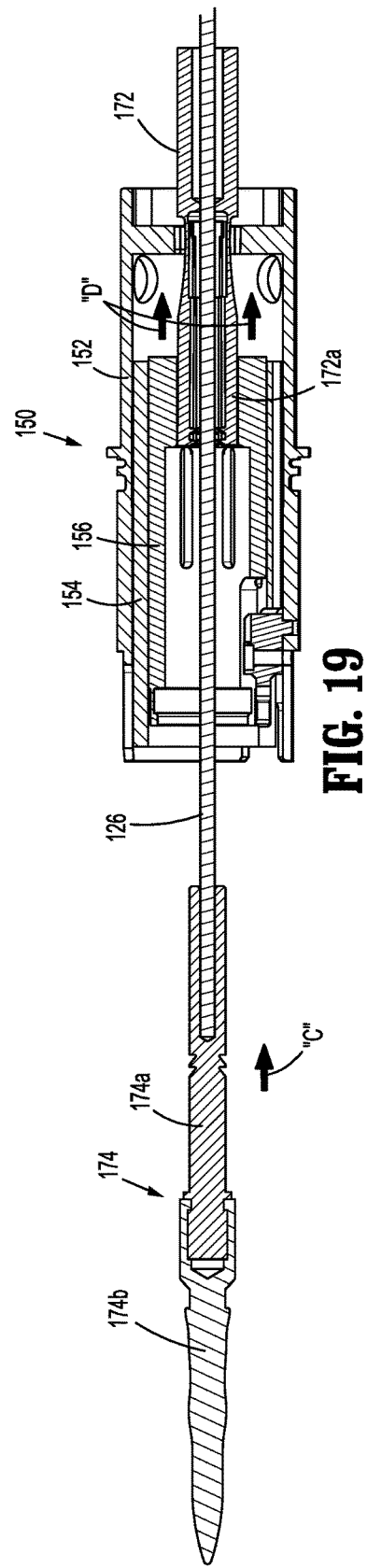
FIG. 18
FIG. 19

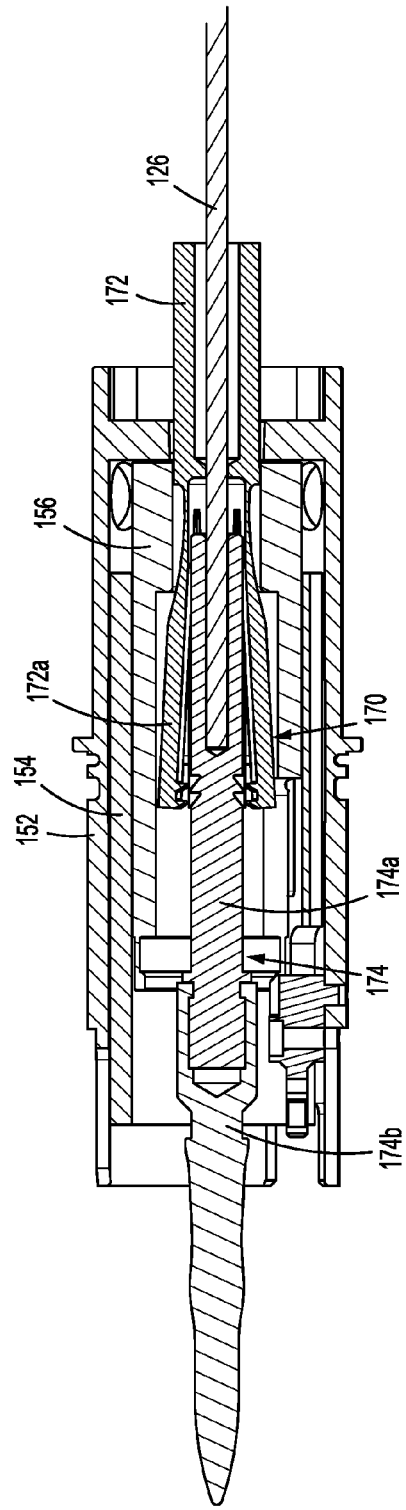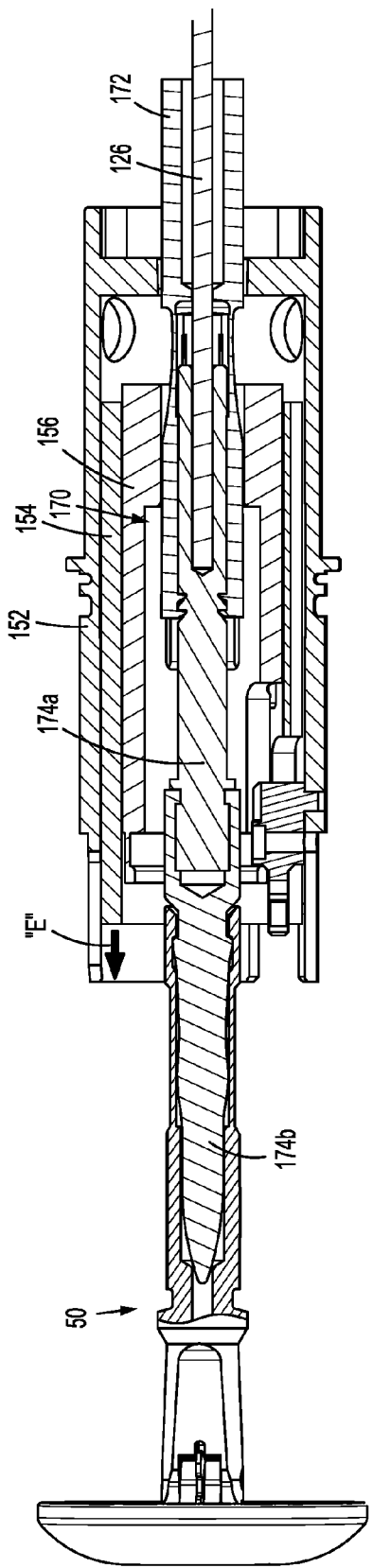
FIG. 20
FIG. 21

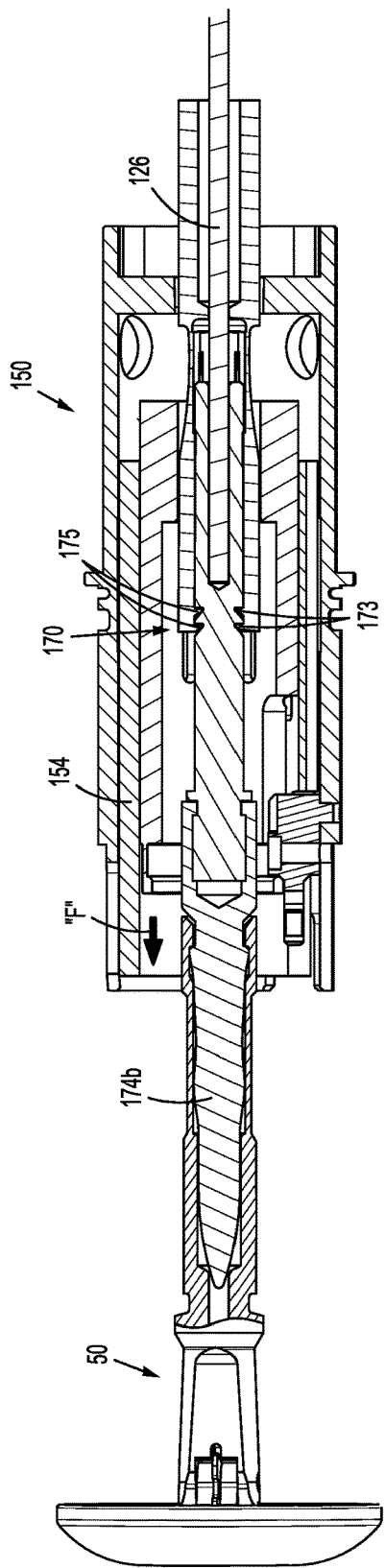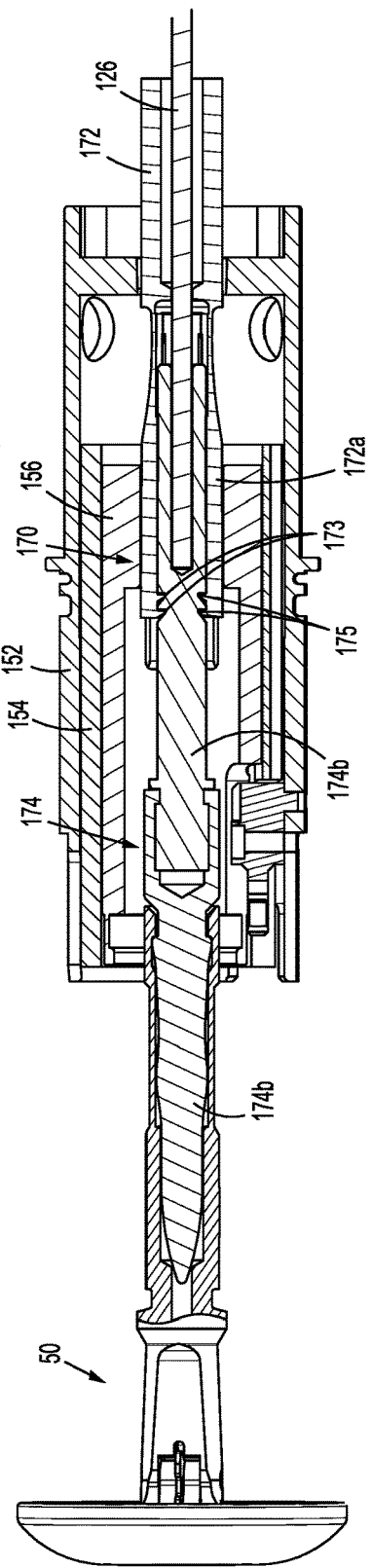

ADAPTER ASSEMBLY FOR SURGICAL DEVICE

CROSS-REFERENCE TO RELATED APPLICATIONS

This application claims the benefit of and priority to U.S. Provisional Patent Application No. 62/251,300 filed Nov. 5, 2015, the entire disclosure of which is incorporated by reference herein.

BACKGROUND

1. Technical Field

The present disclosure relates generally to powered surgical devices. More specifically, the present disclosure relates to adapter assemblies for selectively connecting end effectors to actuation units of powered surgical devices.

2. Background of Related Art

Powered devices for use in surgical procedures typically convert rotational motion from a handle assembly to linear motion for effectuating one or more functions, e.g., clamping, stapling, cutting. To permit reuse of the handle assemblies of these powered surgical devices and so that the handle assembly may be used with a variety of end effectors, adapter assemblies have been developed for selective attachment to the handle assemblies and to a variety of end effectors. Following use, the adapter assembly may be disposed of along with the end effector.

It has been discovered that a need exists for an adapter assembly having a flexible or more flexible body portion, as compared to prior adapter assemblies having rigid or relatively more rigid body portions thereof.

SUMMARY

An adapter assembly for operably connecting an end effector to a powered surgical instrument is provided. The adapter assembly includes a drive coupling assembly, a first drive assembly, a second drive assembly, and an actuation assembly. The first drive assembly is operably connected to the drive coupling assembly and includes a first push/pull cable. The second drive assembly is operably connected to the drive coupling assembly and includes second and third push/pull cables. The actuation assembly includes a first pusher member. Retraction of the second and third push/pull cables effects advancement of the first pusher member.

In embodiments, the adapter assembly further includes a third drive assembly operably connected to the drive coupling assembly. The third drive assembly includes at least fourth and fifth push/pull cables. The actuation assembly may include a second pusher member. Retraction of the fourth and fifth push/pull cables may effect advancement of the second pusher member. The adapter assembly may further include a trocar member. The first push/pull cable may be secured to the trocar member. Each of the second and third push/pull cables and the fourth and fifth push/pull cables may include a corresponding sheath. The second, third, fourth, and fifth push/pull cables and the corresponding sheaths may each include service slack. Each of the second and third push/pull cables may be secured to a first pair of guide members and the fourth and fifth push/pull cables may be secured to a second pair of guide members.

The actuation assembly may include a cylindrical housing. Each guide member of the first and second pairs of guide members may be secured relative to the cylindrical housing. Each of the first, second, and third drive assemblies may include a transmission for converting high speed, low torque input to low speed, high torque output.

The coupling assembly may connect each of the first, second, and third drive assemblies with respective first, second, and third drive shafts of a handle assembly. The first drive assembly may include a first carriage assembly and the second drive assembly may include a second carriage assembly. The first push/pull cable may be secured to the first carriage assembly and the second and third push/pull cables may be secured to the second carriage assembly. The third drive assembly may include a third carriage assembly. The fourth and fifth push/pull cables may be secured to the third carriage assembly.

In embodiments, the adapter assembly further includes a trocar assembly. The trocar assembly may include a locking member and a releasable trocar member. The releasable trocar member may be configured for operable engagement with an anvil assembly.

Also provided is a surgical assembly for connection to and operation by a handheld electromechanical instrument. The surgical assembly includes a trocar assembly and an adapter assembly. The trocar assembly includes a locking member, and a trocar member releasably secured to the locking member. The adapter assembly is configured to be releasably secured to a handheld electromechanical instrument and includes a first drive cable. The locking member of the trocar assembly is secured to the first drive cable and is movable between a first position where the trocar member is releasable from the locking member and a second position were the trocar member is secured to the locking member.

BRIEF DESCRIPTION OF THE DRAWINGS

Embodiments of the present disclosure are described herein with reference to the accompanying drawings, wherein:

FIG. 3 is a perspective end view of a proximal end of the adapter assembly of FIG. 1;

FIG. 4 is a perspective view of a distal end of the adapter assembly of FIG. 1, including the exemplary tool assembly;

FIG. 5 is a perspective end view of the proximal end of the adapter assembly of FIG. 3, with an outer housing removed;

FIG. 6 is another perspective view of the proximal end of the adapter assembly of FIG. 3;

FIG. 13 is a side cross-sectional perspective view of a distal end of the adapter assembly of FIG. 1;

FIG. 14 is an enlarged view of the indicated area of detail in FIG. 13;

FIG. 16 is a side perspective view of the actuation assembly of the adapter assembly of FIG. 15, including the first and second pusher members in their first or proximal positions;

FIG. 17 is a side perspective view of the actuation assembly of the adapter assembly of FIG. 15, including the second pusher member;

FIG. 18 is a side perspective view of a locking member and a trocar member of a trocar assembly of the adapter assembly of FIG. 1, with parts separated;

FIG. 19 is a cross-sectional side view of the actuation assembly of the adapter assembly of FIG. 15, with the trocar assembly in an extended condition;

FIG. 20 is a cross-sectional side view of the actuation assembly of FIG. 19, with the trocar assembly in a retracted position;

FIG. 21 is a cross-sectional side view of the actuation assembly of FIG. 19 and the anvil assembly of FIG. 1, with the second pusher member in a first distal position;

FIG. 22 is a cross-sectional side view of the actuation assembly of FIG. 19, with the first pusher member in its distal-most position; and FIG. 23 is a cross-sectional side view of the actuation assembly of FIG. 19, with the first and second pusher members in their distal-most position.

DETAILED DESCRIPTION OF EMBODIMENTS

Figure 1:
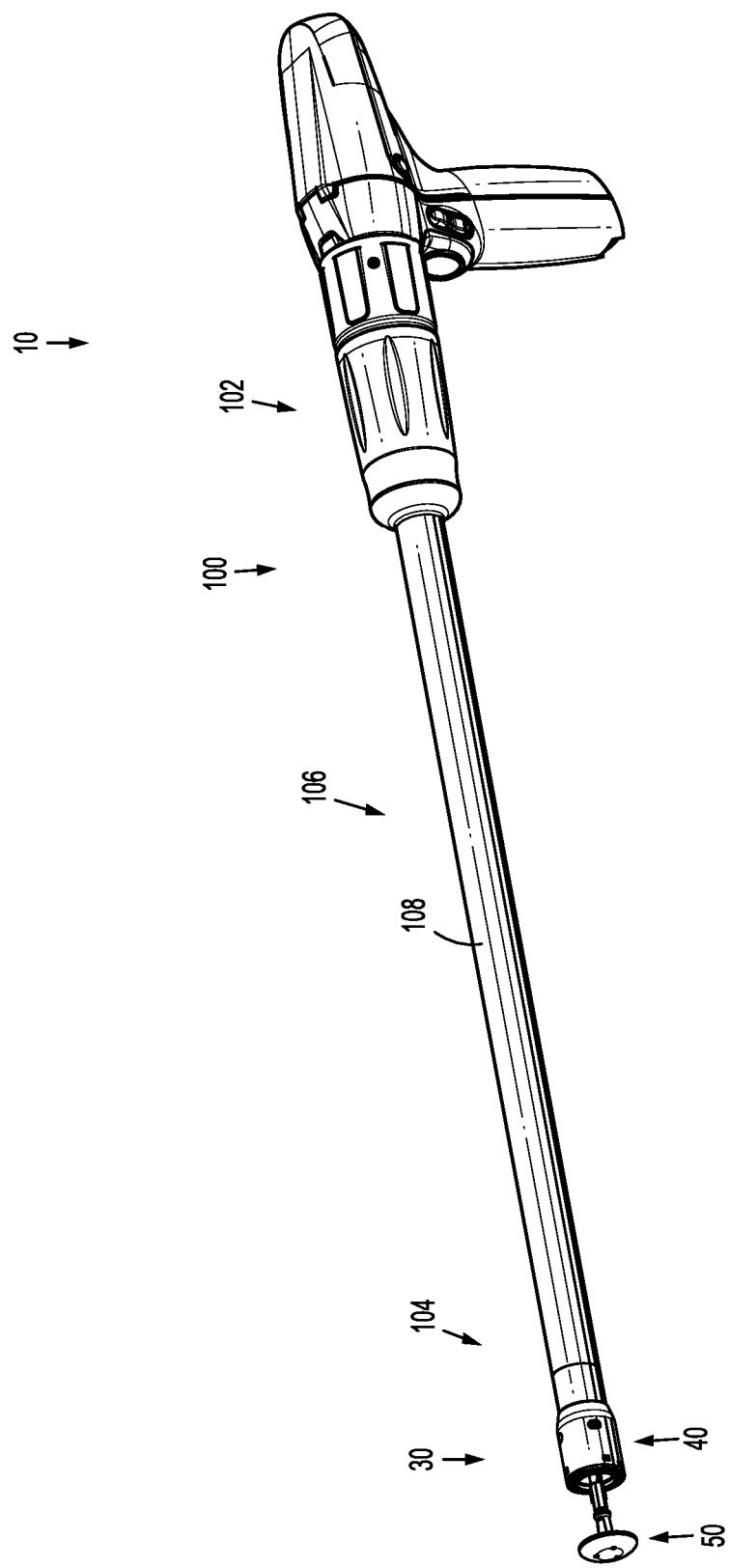
FIG. 1 is a perspective view of an adapter assembly, in accordance with an embodiment of the present disclosure, an exemplary handle assembly, and an exemplary tool assembly.

Embodiments of the presently disclosed adapter assembly for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Figure 2:
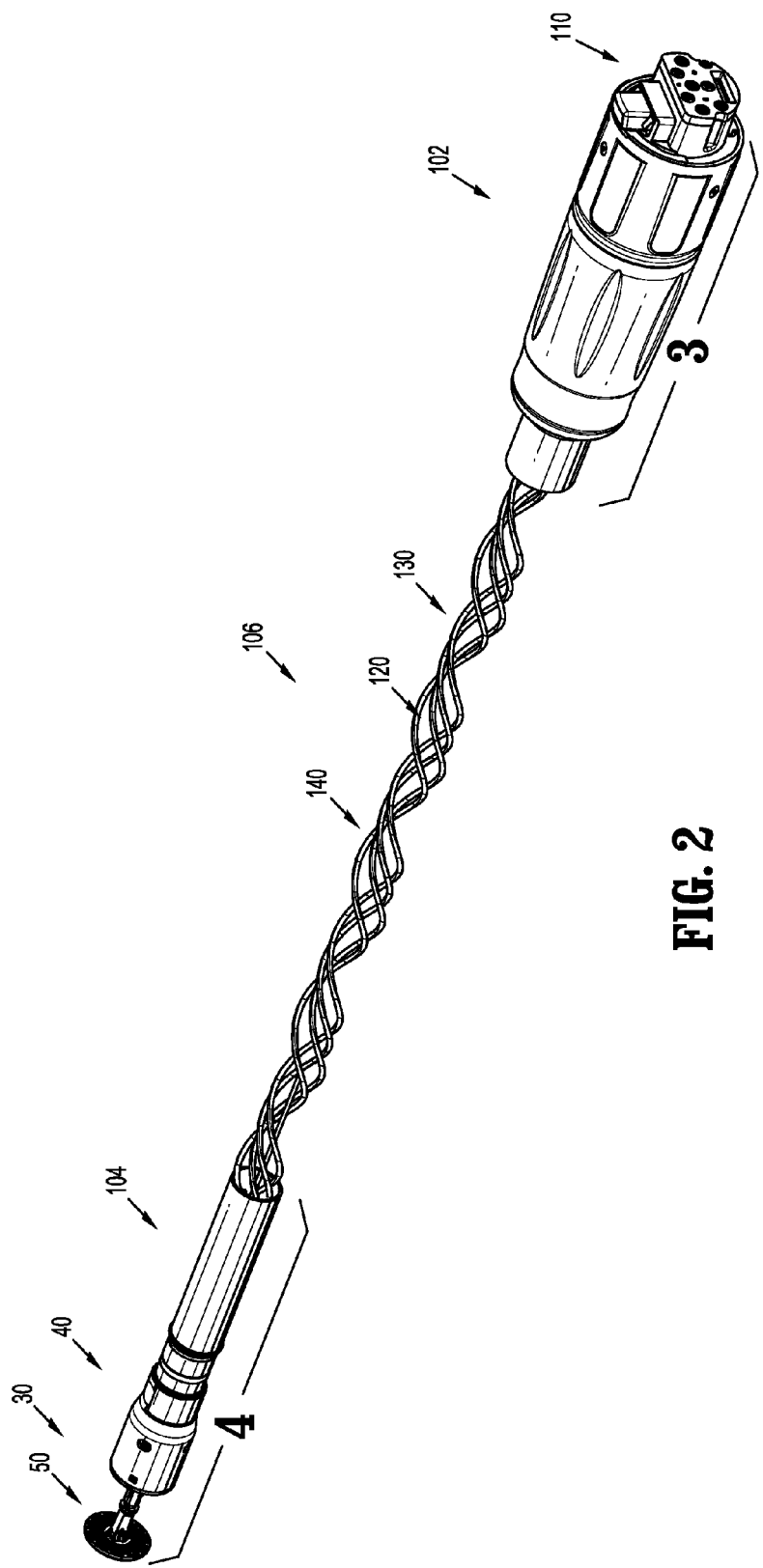
FIG. 2 is a perspective view of the adapter assembly of FIG. 1 including the exemplary tool assembly, with an outer sleeve removed.

With reference to FIGS. 1 and 2, an adapter assembly in accordance with an embodiment of the present disclosure, shown generally as adapter assembly 100, is configured for selective connection to a powered handheld electromechanical instrument shown, generally as handle assembly 20. As illustrated in FIG. 1, the handle assembly 20 is configured for selective connection with the adapter assembly 100, and, in turn, the adapter assembly 100 is configured for selective connection with a tool assembly or end effector, e.g. tool assembly 30, which may, in exemplary embodiments, include a loading unit 40 and an anvil assembly 50, for applying a circular array of staples (not shown) to tissue (not shown). The handle assembly 20, along with the adapter assembly 100 and the tool assembly 30 form a surgical stapling device 10. Although shown and described for use with a circular stapling loading unit, it is envisioned that the aspects of the present disclosure may be modified for use with stapling assembly have alternative configurations.

For a detailed description of the structure and function of an exemplary handle assembly, please refer to commonly owned U.S. Pat. Appl. Publ. Nos. 2012/0253329, 2015/0157320, and 2015/0157321 ("the '329, '320, and '321 applications"), the content of each of which is incorporated by reference herein in its entirety.

With continued reference to FIGS. 2-4, the adapter assembly 100 includes a proximal portion 102 (FIG. 3) configured for operable connection to the handle assembly 20 (FIG. 1), a distal portion 104 configured for operable connection to the tool assembly 30 (FIG. 1), and an intermediate portion 106 operably connecting the proximal and distal portions 102, 104. The proximal portion 102 of the adapter assembly 100 includes a coupling assembly 110 receivable within the handle assembly 20 (FIG. 1) for operatively connecting first, second, and third drive shafts (not shown) of the handle assembly 20 with the adapter assembly 100, and a drive assembly 115 (FIG. 5) for transferring power from the handle assembly 20 to the tool assembly 30. For a detailed description of an exemplary adapter assembly including an exemplary coupling assembly, please refer to commonly owned U.S. patent application Ser. No. 14/875,766 ("the '766 application"), filed Oct. 21, 2014, the contents of which are incorporated herein by reference in their entirety, and the previously incorporated '329, '320, and '321 applications.

With reference to FIGS. 5-9, first, second, and third drive assemblies 120 (FIGS. 7 and 8), 130, 140 of the adapter assembly 100 extend from the coupling assembly 110, through an outer sleeve 108 (FIG. 1) of the intermediate portion 106 (FIG. 1), and to an actuation assembly 150 (FIG. 10) disposed in the distal portion 104 (FIG. 4) of the adapter assembly 100. As will be described in further detail below, the first drive assembly 120 operates to effect a first function, e.g., clamping of tissue, of the tool assembly 30 (FIG. 1). The second drive assembly 130 operates to effect a second function, e.g., stapling of tissue, of the tool assembly 30 (FIG. 1). The third drive assembly 140 operates to effect a third function, e.g., cutting of tissue, of the tool assembly 30 (FIG. 1).

The first drive assembly 120 extends through the proximal and intermediate portions 102, 106 (FIG. 2) of the adapter assembly 100 and includes a first elongate drive shaft 122 rotatably supported within the proximal portion 102 of the adapter assembly 100, a first carriage assembly 124 movably supported by the first elongate drive shaft 122, and a first push/pull cable 126 (FIG. 8) secured to the first carriage assembly 124. The first push/pull cable 126 extends from the first carriage assembly 124 through the intermediate portion 106 (FIG. 2) to the actuation assembly 150 (FIG. 10) in the distal portion 104 (FIG. 4) of the adapter assembly 100.

Figure 9:
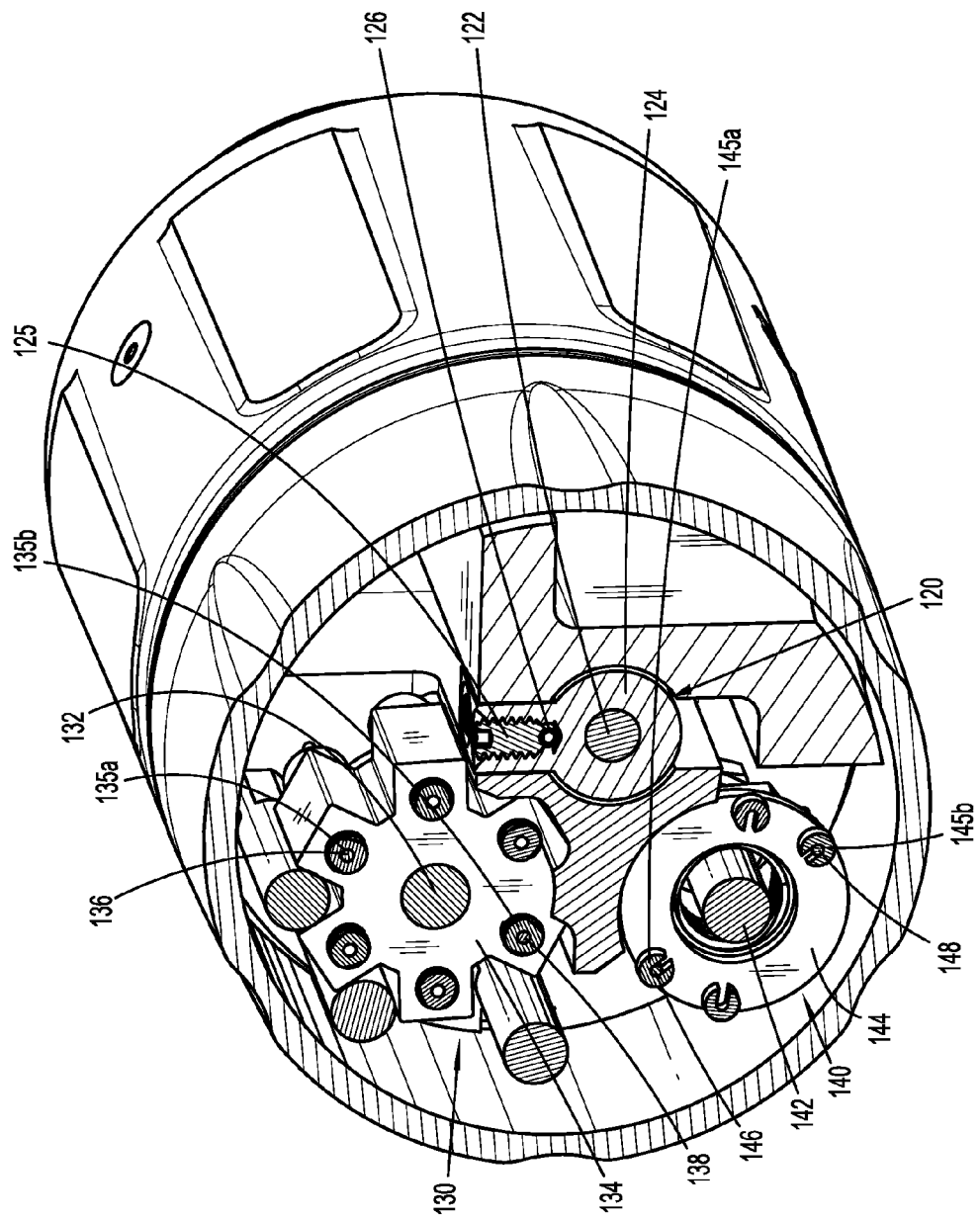
FIG. 9 is a cross-sectional perspective end view of the proximal end of the adapter assembly of FIG. 8, taken along section line 9-9.

With particular reference to FIG. 9, the first carriage assembly 124 of the first drive assembly 120 is in threaded engagement (not shown) with the first elongate drive shaft 122 of the first drive assembly 120, such that rotation of the first elongate drive shaft 122 causes longitudinal movement, i.e., advancement and retraction, of the first carriage assembly 124. Longitudinal movement of the first carriage assembly 124 of the first drive assembly 120 pushes and pulls the first push/pull cable 126 to effect longitudinal movement, i.e., advancement and retraction, of a trocar member 174 (FIG. 18) of a trocar assembly 170 (FIG. 18) disposed in the distal portion 104 (FIG. 4) of the adapter assembly 100. The first push/pull cable 126 is adjustably secured to the first carriage assembly 124 by a set screw 125 (FIG. 9). The effective length of the first push/pull cable 126 may be adjusted using the set screw 125 to accommodate, for example, anvil assemblies of different sizes.

The second drive assembly 130 extends through the proximal and intermediate portions 102, 106 (FIG. 2) of the adapter assembly 100 and includes a second elongate drive shaft 132 rotatably supported within the proximal portion 102 of the adapter assembly 100, a second carriage assembly 134 movably supported along the second elongate drive shaft 132, and second and third push/pull cables 136, 138 secured to the second carriage assembly 134. Although shown including two (2) push/pull cables, the second carriage assembly 134 is configured to accommodate up to six (6) push/pull cables. It is envisioned that the second carriage assembly 134 may be configured to accommodate any number of push/pull cables. In some embodiments, the second and third push/pull cables 136, 138 are small coiled throttle cables which are capable of handling large compressive loads without buckling while remaining flexible. The second and third push/pull cables 136, 138 are adjustably secured to the second carriage assembly 134 by set screws 135. The effective length of the second and third push/pull cable 136, 138 may be adjusted using the set screws 135 to accommodate, for example, loading units having various sized pusher assemblies.

With particular reference to FIG. 9, the second carriage assembly 134 of the second drive assembly 130 is in threaded engagement (not shown) with the second elongate drive shaft 132 of the second drive assembly 130, such that rotation of the second elongate drive shaft 132 causes longitudinal movement, i.e., advancement and retraction, of the second carriage assembly 134. Longitudinal movement of the second carriage assembly 134 pushes and pulls the second and third push/pull cables 136, 138 to effect longitudinal movement, i.e., advancement and retraction, of a first pusher member 154 (FIG. 16) of the actuation assembly 150 (FIG. 10) disposed in the distal portion 104 of the adapter assembly 100.

The third drive assembly 140 extends through the proximal and intermediate portions 102, 106 (FIG. 2) of the adapter assembly 100 and includes a third elongate drive shaft 142 rotatably supported within the proximal portion 102 of the adapter assembly 100, a third carriage assembly 144 movably supported along the third elongate drive shaft 142, and fourth and fifth push/pull cables 146, 148 secured to the third carriage assembly 144. Although shown including only two (2) push/pull cables 146, 148, the third carriage assembly 144 is configured to accommodate up to four (4) push/pull cables. It is envisioned that the third carriage assembly 144 may be configured to accommodate any number of push/pull cables. In some embodiments, the fourth and fifth push/pull cables 146, 148 are small coiled throttle cables which are capable of handling large compressive loads without buckling while remaining flexible. The fourth and fifth push/pull cables 146, 148 are adjustably secured to the second carriage assembly 144 by set screws 145. The effective length of the fourth and fifth push/pull cables 146, 148 may be adjusted using the set screws 145 to accommodate, for example, loading units having various sized pusher assemblies.

With particular reference to FIG. 9, the third carriage assembly 144 of the third drive assembly 140 is in threaded engagement (not shown) with the third elongate drive shaft 142 of the third drive assembly 140, such that rotation of the third elongate drive shaft 142 causes longitudinal movement, i.e., advancement and retraction, of the third carriage assembly 144. Longitudinal movement of the third carriage assembly 144 pushes and pulls the fourth and fifth push/pull cables 146, 148 to effect longitudinal movement, i.e., advancement and retraction, of a second pusher member 156 (FIG. 17) of the actuation assembly 150 (FIG. 10) disposed in the distal portion 104 of the adapter assembly 100.

Figure 7:
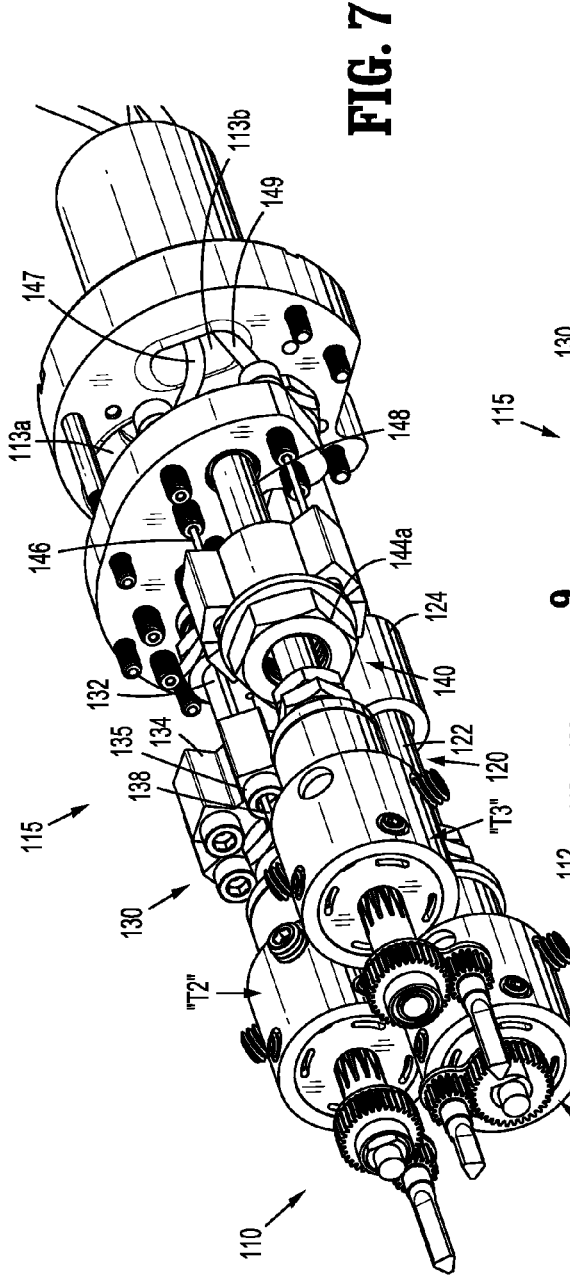
FIG. 7 is a perspective end view of the proximal end of the adapter assembly of FIG. 3, with the outer housing and an inner housing removed.
Figure 8:
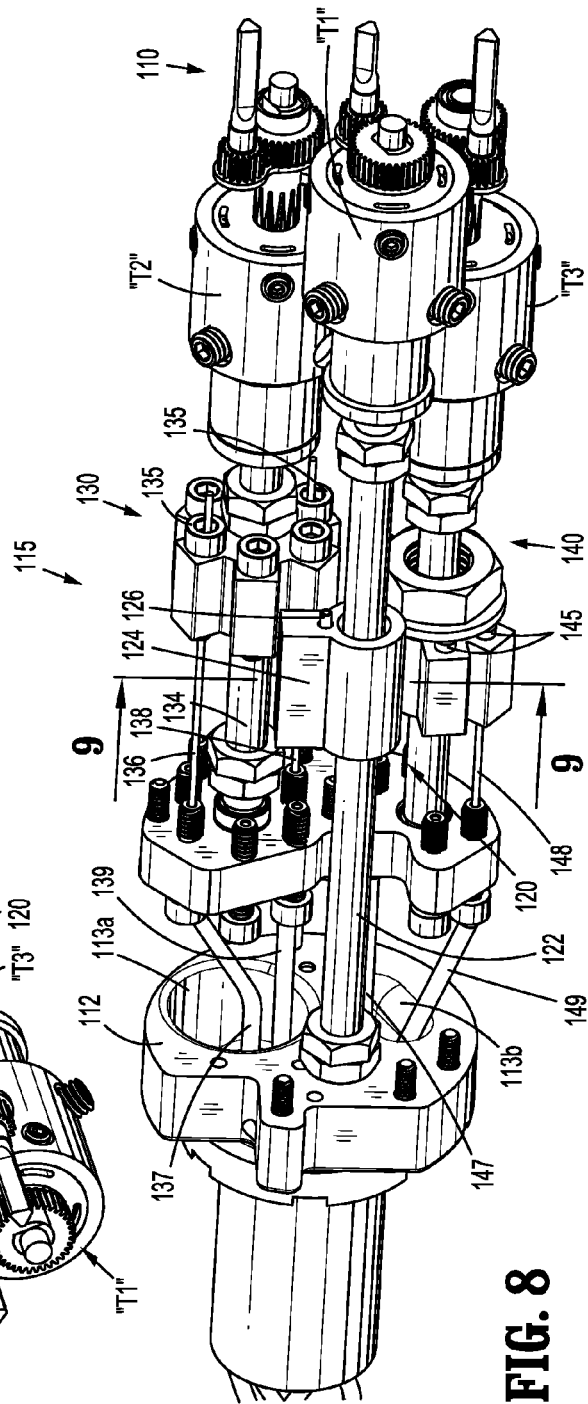
FIG. 8 is another perspective view of the proximal end of the adapter assembly of FIG. 7.

With particular reference to FIGS. 7 and 8, disposed between the coupling assembly 110 of the adapter assembly 100 and the first elongate drive shaft 122 of the first drive assembly 120 of the adapter assembly 100 is a first high ratio transmission assembly "T1". Disposed between the coupling assembly 110 of the adapter assembly 100 and the second elongate drive shaft 132 of the second drive assembly 130 of the adapter assembly 100 is a second high ratio transmission assembly "T2". A third high ratio transmission assembly "T3" is disposed between the coupling assembly 110 of the adapter assembly 100 and the third elongate drive shaft 142 of the adapter assembly 100. The first, second, and third high ratio transmission assemblies "T1", "T2", "T3" convert the high speed, low torque rotary input from the handle assembly 20 (FIG. 1) to lower speed, higher torque output for use in effecting actuation of the tool assembly 30 (FIG. 1). Although shown as planetary gear systems, each of the first, second, and third high ratio transmission assemblies "T1", "T2", "T3", may be any type of suitable high ratio transmission assembly, e.g., orbital gear system, yoked sun orbital gear system, compound gear system. For a detailed description of an exemplary planetary gear system, please refer to the '766 application, the content of which was previously incorporated by reference herein.

With continued reference to FIGS. 5-9, the second and third push/pull cables 136, 138 of the second drive assembly 130 extend through a first opening 113a in a frame member 112 of the proximal portion 104 of the adapter assembly 100, and the fourth and fifth push/pull cables 146, 148 extend through a second opening 113b in the frame member 112. Each of the second, third, fourth, and fifth push/pull cables 136, 138, 146, 148 includes an outer sheath or service conduit 137, 139, 147, 149, respectively. As noted above, proximal ends of the second and third cables 136, 138 are secured to the second carriage assembly 134 and proximal ends of the fourth and fifth cables 146, 148 are secured to the third carriage assembly 144. Similarly, proximal ends of the respective second, third, fourth, and fifth outer sheaths 137, 139, 147, 149 of the respective second, third, fourth, and fifth push/pull cables 136, 138, 146, 148 are secured to the frame member 112.

Figure 10:
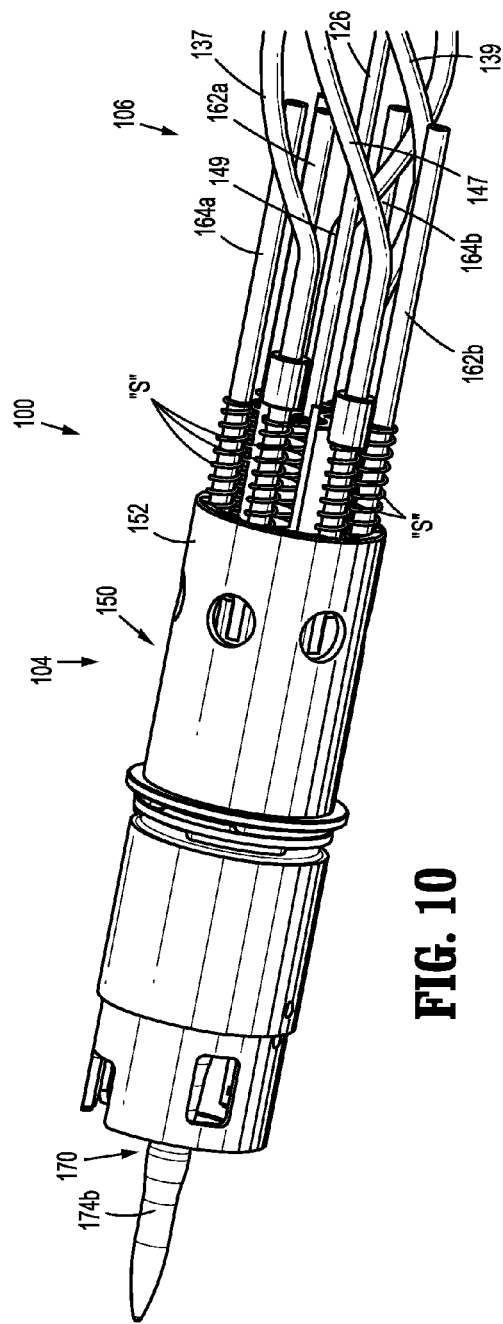
FIG. 10 is a side perspective view of the distal end of the adapter assembly shown in FIG. 4, with the outer sleeve removed.

With additional reference to FIG. 10, the first push/pull cable 126 of the first drive assembly 120, and each of the second, third, fourth, and fifth push/pull cables 136, 138, 146, 148 with respective outer sheaths 137, 139, 147, 149 of the second and third drive assemblies 130, 140, respectively, extend through the intermediate portion 106 (FIG. 1) of the adapter assembly 100 and operably engage the actuation assembly 150 disposed in the distal portion 104 of the adapter assembly 100.

Figure 11:
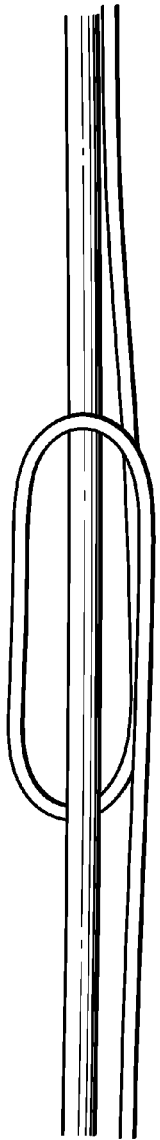
FIG. 11 is a side perspective view of a pair of push/pull cables having a wave configuration.
Figure 12:
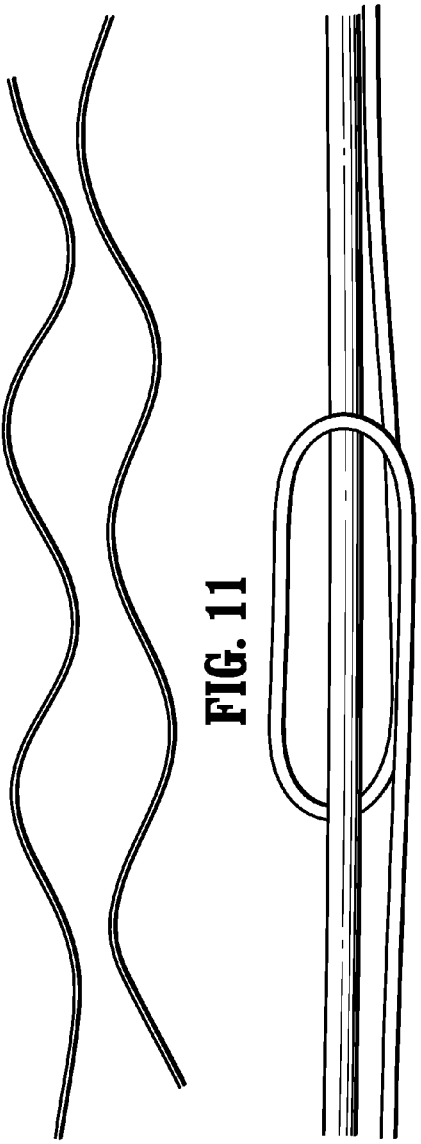
FIG. 12 is a side perspective view of a push/pull cable having a looped configuration.
Figure 15:
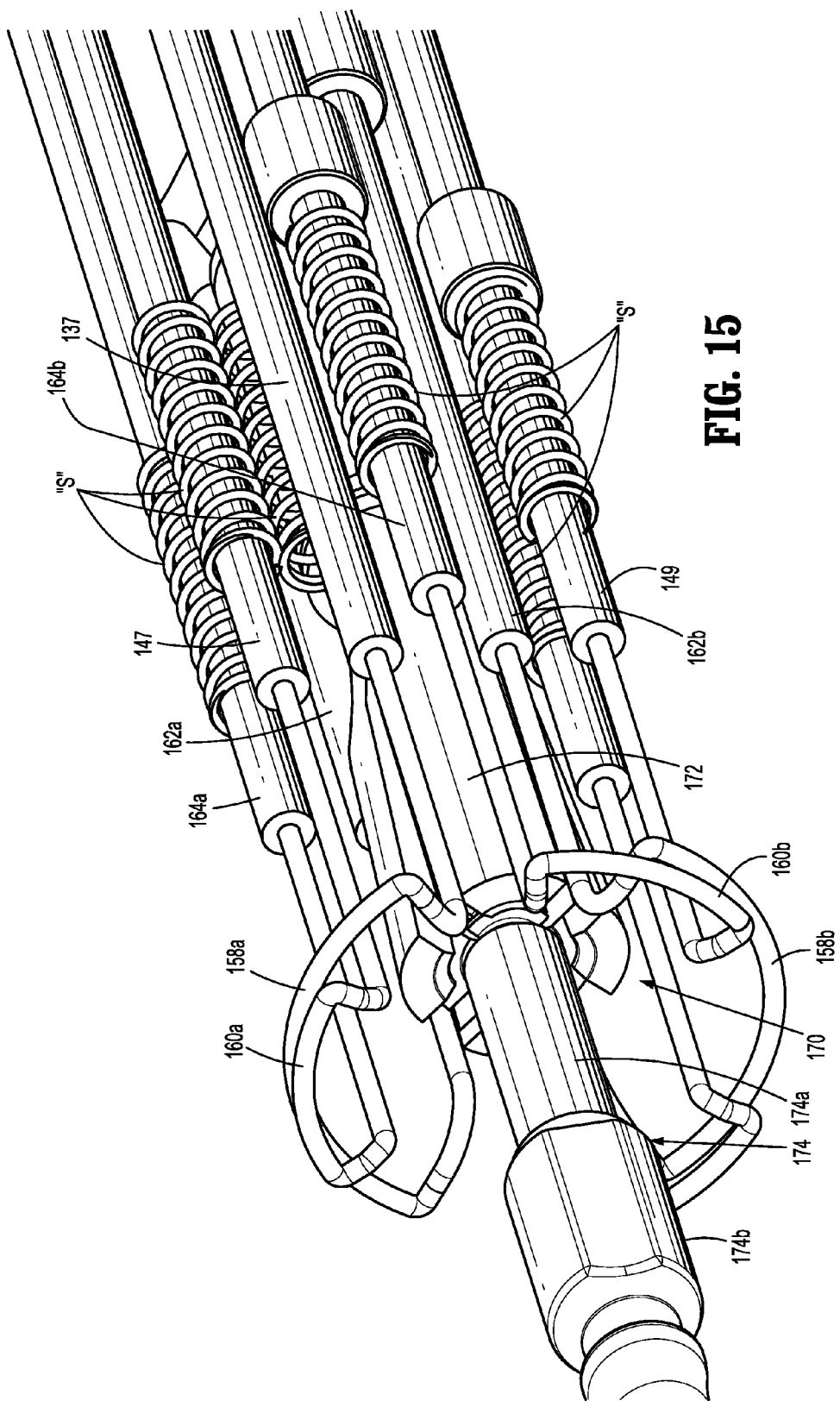
FIG. 15 is a perspective view of an actuation assembly of the adapter assembly of FIG. 1, with a housing, and first and second pusher members removed.

As shown in FIG. 10, the second, third, fourth, and fifth push/pull cables 136, 138, 146, 148 are arranged in a helical pattern within the intermediate portion 106 of the adapter assembly 100. It is envisioned that the second, third, fourth, and fifth push/pull cables 136, 138, 146, 148 may instead be arranged in a wave pattern (FIG. 11), an offset wave pattern, or simple loop pattern (FIG. 12). These arrangements provide service slack, i.e., extra length, in the second, third, fourth, and fifth push/pull cables 136, 138, 146, 148 of the respective second and third drive assemblies 130, 140 within the intermediate portion 106 of the adapter assembly 100. In addition to accommodating the shortening and lengthening of the intermediate portion 106 of the adapter assembly during flexing of the adapter assembly 100, the service slack allows for migration during cycling operation of the second and third drive assemblies 130, 140.

As will be described in further detail below, the inclusion of the service slack in each of the second, third, fourth, and fifth push/pull cables 136, 138, 146, 148 and the respective second, third, fourth, and fifth outer sheaths 137, 139, 147, 149 within the intermediate portion 106 of the adapter assembly 100 changes the relative frame of reference of the second, third, fourth, and fifth push/pull cables 136, 138, 146, 148 and the respective second, third, fourth, and fifth outer sheaths 137, 139, 147, 149. The configuration of the adapter assembly 100 is such that when the second, third, fourth, and fifth push/pull cables 136, 138, 146, 148 are pulled within the proximal portion 102 of the adapter assembly 100, the second, third, fourth, and fifth outer sheaths 137, 139, 147, 149 of the respective second, third, fourth, and fifth push/pull cables 136, 138, 146, 148 are pushed within the distal portion 104 of the adapter assembly 100.

With reference now to FIGS. 13-17, the actuation assembly 150 of the adapter assembly 100 includes a cylindrical housing 152 received within an inner sleeve 108a of the distal portion 104 of the adapter assembly 100, the first and second pusher members 154, 156 slidably supported within the cylindrical housing 152, first and second pairs of guide members 158a, 158b, 160a, 160b secured relative to the cylindrical housing 152, and first and second pairs of guide tubes 162a, 162b, 164a, 164b (FIG. 10) extending from respective first and second pusher members 154, 156 and about respective free ends of the first and second pairs of guide members 158a, 158b, 160a, 160b.

With particular reference to FIG. 13, a proximal end of the cylindrical housing 152 of the actuation assembly 150 extends from a distal end of the inner sleeve 108a and both the cylindrical housing 152 and the inner sleeve 108a are received within a distal end of the outer sleeve 108 (FIG. 1). A distal end of the cylindrical housing 152 releasably receives the loading unit 40 of the tool assembly 30 (FIG. 2).

With continued reference to FIGS. 13-17, the first pusher member 154 of the actuation assembly 150 is movably supported within the cylindrical housing 152 (FIG. 13) of the actuation assembly 150 and the second pusher member 156 is moveably supported within the first pusher member 154. The second and third outer sheaths 137, 139 (FIG. 16) of the respective second and third push/pull cables 136, 138 (FIG. 9) engage the first pusher member 154 (FIG. 16) and the fourth and fifth outer sheaths 147, 149 (FIG. 17) of the respective fourth and fifth push/pull cables 136, 148 (FIG. 9) engage the second pusher member 156 (FIG. 17). The first and second pusher members 154, 156 each define a plurality of slots 153 (FIG. 16), 155 (FIG. 17), respectively, for accommodating the first and second pairs of guide members 158a, 158b, 160a, 160b.

As noted above, each of the first pair of guide members 158a, 158b is integrally formed with, or securely connected to, the respective second and third push/pull cable 136, 138 (FIG. 9), of the second drive assembly 130 of the adapter assembly 100. Each guide member 158a, 158b of the first pair of guide members engages the cylindrical housing 152 of the actuation assembly 150 (see, for example, FIG. 14) to fix the second and third push/pull cables 136, 138 relative to the actuation assembly 150. A free end of each of guide member 158a, 158b of the first pair of guide members is received within the respective tubular guide 162a, 162b extending from the first pusher member 154. As noted above, the second drive assembly 130 includes two (2) push/pull cables 136, 138, however, the second drive assembly 130 is capable of accommodating up to six (6) push/pull cables (not shown). In some embodiments, any or all of the tubular guides 162a, 162b may be replaced with additional push/pull cables (not shown) and accompanying outer sheaths (not shown).

During actuation of the second drive assembly 130, each of the second and third push/pull cables 136, 138 are retracted through longitudinal movement of the second carriage assembly 134 of the second drive assembly 130. As described in detail above, the configuration of the second and third push/pull cables 136, 138 of the second drive assembly 130, and the accompanying second and third sheaths 137, 139, respectively, facilitated by the service slack provided by, for example, the helical pattern of the second and third push/pull cables 136, 138 within the intermediate portion 106 of the adapter assembly 100, is such that when the second and third push/pull cables 136, 138 are pulled, i.e., retracted, the second and third sheaths 137, 139 move distally, i.e., advance. Advancement of the second and third sheaths 137, 139 of the second drive assembly 130 causes distal movement of the first pusher member 154 of the actuation assembly 150, as indicated by arrow "A" in FIG. 16.

As noted above, each guide member 160a, 160b of the second pair of guide members is integrally formed with, or securely connected to, the respective fourth and fifth push/pull cable 146, 148, of the third drive assembly 140 of the adapter assembly 100. Each guide member 160a, 160b of the second pair of guide members engages the cylindrical housing 152 of the actuation assembly 150 to fix the fourth and fifth push/pull cables 146, 148 relative to the actuation assembly 150. The free end of each guide member 160a, 160b of the second pair of guide members is received within the respective tubular guide 164a, 164b extending for the second pusher member 156. As noted above, the third drive assembly 140 includes two (2) push/pull cables 146, 148; however, the third drive assembly 140 is capable of accommodating up to four (4) push/pull cables. In some embodiments, any or all of the tubular guides 164a, 164b may be replaced with additional push/pull cables (not shown) and accompanying outer sheaths (not shown).

During actuation of the third drive assembly 140, each of the fourth and fifth push/pull cables 146, 148 are retracted through longitudinal movement of the third carriage assembly 144 of the third drive assembly 140. As described in detail above, the configuration of the fourth and fifth push/pull cables 146, 148, and the accompanying fourth and fifth sheaths 147, 149, respectively, facilitated by the service slack provided by the, for example, helical pattern (FIG. 2) of the fourth and fifth push/pull cables 146, 148 within the intermediate portion 106 of the adapter assembly 100, is such that when the fourth and fifth push/pull cables 146, 148 are pulled, i.e., retracted, the fourth and fifth sheaths 147, 149 are moved distally, i.e., advanced. Advancement of the fourth and fifth sheaths 147, 149 of the third drive assembly 140 causes distal movement of the second pusher member 156 of the actuation assembly 150, as indicated by arrow "B" in FIG. 16.

Springs "S" received about the second, third, fourth, and fifth sheaths 137, 139, 147, 149 of the respective second, third, fourth, and fifth push/pull cables 136, 138, 146, 148 facilitate the return of the second, third, fourth, and fifth sheaths 137, 139, 147, 149 to their initial positions when the respective second, third, fourth, and fifth push/pull cables 136, 138, 146, 148 are advanced, i.e., pushed distally. As the second, third, fourth, and fifth sheaths 137, 139, 147, 149 move proximally, the respective first and second pusher members 154, 156 are moved distally, i.e., retracted.

When the loading unit 40 is secured to the cylindrical housing 152 of the actuation assembly 150, the first pusher member 154 engages a staple pusher member 42 of the loading unit 40 and the second pusher member 156 engages a knife pusher member 44 of the loading unit 40. The first and second pusher members 154, 156 are moveably supported within the cylindrical housing 152 to effect longitudinal movement of the respective stapler pusher member 42 and the knife pusher member 44.

With reference now to FIGS. 18-23, the trocar assembly 170 of the adapter assembly 100 is operably connected to the first drive assembly 120 and is operably received through the first and second pusher members 154, 156 of the actuation assembly 150. More particularly, the trocar assembly 170 includes a locking member 172, and a trocar member 174 releasably secured to the locking member 172. The trocar member 174 may be formed of proximal and distal portions 174a, 174b, as shown, or may be integrally formed, e.g., monolithic.

A proximal end of the locking member 172 is securely connected to the first push/pull cable 126 of the first drive assembly 120 (FIG. 8). A distal end of the locking member 172 includes a plurality of fingers 172a configured for releasably engaging the trocar member 174. The plurality of fingers 172a are movable between a first position (FIG. 18) in which the plurality of fingers 172a are splayed apart to facilitate the receipt of the trocar member 174 therein, and a second position (FIG. 21) in which the plurality of fingers 172a are compressed about the trocar member 174 to secure the trocar member 174 therein. As will be described in further detail below, the plurality of fingers 172a are in the first position when the second pusher member 156 of the actuation assembly 150 is in a proximal-most position, thereby allowing the plurality of fingers 172a to splay outwardly.

Each of the plurality of fingers 172a includes a locking feature, e.g., a pair of teeth 173, and the proximal portion 174a of the trocar member 174 defines a corresponding locking feature, e.g., a pair of annular grooves 175. The annular grooves 175 are positioned to receive the pairs of teeth 173 of the plurality of fingers 172a when the trocar member 174 is in engagement with the locking member 172 and the plurality of fingers 172a are in their second position.

With particular reference to FIG. 19, the first drive assembly 120 is shown with the first push/pull cable 126 in a distal-most position. When in the distal-most position, a tissue piercing tip of the distal portion 174b of the trocar member 174 facilitates penetration of tissue (not shown) by the trocar member 174. As shown, the second pusher assembly 156 of the actuation assembly 150 is in its proximal-most position. In this manner, the plurality of fingers 172a of the locking member 172 of the trocar assembly 170 is in its second position.

Turning to FIG. 20, actuation of the first drive assembly 120 causes pulling, i.e., retraction, of the first push/pull cable 126, as indicated by arrow "C" in FIG. 19, to retract the trocar member 174 within the plurality of fingers 172a of the locking member 172 of the trocar assembly 170. Prior to, or simultaneously with the retraction of the first push/pull cable 126, the third drive assembly 140 (FIG. 7) is actuated to cause the retraction of the second pusher member 156, as indicated by arrow "D" in FIG. 19, to its proximal-most position, in the manner described above. Alternatively, the adapter assembly 100 is provided to a clinician with the second pusher member 156 of the actuation assembly 150 in its proximal-most position, thereby eliminating the need to retract the second pusher member 156 prior to securing the trocar member 174 to the locking member 172.

Turning to FIG. 21, upon receipt of the trocar member 174 of the trocar assembly 170 within the locking member 172 of the trocar assembly 170, the second pusher member 156 of the actuation assembly 150 is returned to its initial position, i.e., advanced, through operation of the third drive assembly 140. As the second pusher member 156 advances relative to the locking member 172, engagement between the second pusher member 156 and the plurality of fingers 172a of the locking member 172 causes the plurality of fingers 172a to flex radially inwardly about the proximal portion 174a of the trocar member 174 such that the pairs of teeth 173 of the plurality of fingers 172a of the locking member 172 are received within the annular grooves 175 of the trocar member 174. In this manner, the trocar member 174 is secured to the locking member 172.

With reference to FIG. 22, during operation of the surgical stapling device 10, actuation of the first drive assembly 120 (FIG. 8), in the manner described above, effects movement of the trocar assembly 170, as indicated by arrow "D". When the anvil assembly 50 is secured to the distal portion 174b of the trocar member 174 of the trocar assembly 170, movement of the trocar assembly 170 causes a clamping of tissue between, for example, the anvil assembly 50 (FIG. 1) and the loading unit 40 of the tool assembly 30 (FIG. 1).

Subsequent to the clamping of tissue (not shown), actuation of the second drive assembly 130 (FIG. 8), in the manner described above, effects movement of the first pusher member 154 of the actuation assembly 150, as indicated by arrow "E" in FIG. 21. As noted above, the first pusher member 154 is connected to the staple pusher member 42 (FIG. 13) of the loading unit 40 (FIG. 13). Accordingly, advancement of first pusher member 154 of the actuation assembly 150 causes advancement of the stapler pusher member 42 of the loading unit 40 to effect the stapling of tissue (not shown) that is clamped between the anvil assembly 50 (FIG. 1) and the loading unit 40 of the tool assembly 30 (FIG. 1).

Turning to FIG. 23, subsequent to the stapling of tissue (not shown), actuation of the third drive assembly 140, in the manner described above, effects movement of the second pusher member 156 of the actuation assembly 150, as indicated by arrow "F" in FIG. 22. As noted above, the second pusher member 156 is connected to the knife pusher member 44 (FIG. 13) of the loading unit 40 (FIG. 13). Accordingly, advancement of second pusher member 156 of the actuation assembly 150 causes advancement of the knife pusher member 44 of the loading unit 40 to effect the cutting of tissue (not shown) that is clamped between anvil assembly 50 (FIG. 1) and the loading unit 40 of the tool assembly 30 (FIG. 1).

Although the adapter assembly 100 has been shown and described in relation to operation of the tool assembly 30 (FIG. 1) including the loading unit 40 (FIG. 1) and the anvil assembly 50 (FIG. 1), the adapter assembly 100 may be modified for operation with end effectors having different configurations. For example, the adapter assembly 100 may be modified for use with an end effector having only a single actuation, e.g., linear stapling.

Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to a surgical instrument, the adapter assembly comprising:
   an outer housing having proximal and distal portions;
   a drive coupling assembly disposed in the proximal portion of the outer housing;
   a first drive assembly operably connected to the drive coupling assembly, the first drive assembly including a first push/pull cable;
   a second drive assembly operably connected to the drive coupling assembly, the second drive assembly including at least second and third push/pull cables, each of the at least second and third push/pull cables including a service slack and an outer sheath having proximal and distal portions;
   a frame member disposed within the outer housing, wherein the proximal portions of the outer sheaths of the at least second and third push/pull cables are secured to the frame member;
   an actuation assembly including a first pusher member and an inner housing, the first pusher member being movably supported within the inner housing, the distal portions of the outer sheaths of the at least second and third push/pull cables being secured to the first pusher member, wherein each of the second and third push/pull cables are secured to the inner housing by a first pair of guide members; and
   wherein retraction of the second and third push/pull cables effects advancement of the first pusher member.

2. The adapter assembly of claim 1, further including a third drive assembly operably connected to the drive coupling assembly, the third drive assembly including at least fourth and fifth push/pull cables secured relative to the inner housing, each of the at least fourth and fifth push/pull cables including a service slack and an outer sheath having proximal and distal portions.

3. The adapter assembly of claim 2, wherein the actuation assembly includes a second pusher member, the second pusher member being movably supported within the inner housing, the distal portions of the outer sheaths of the at least fourth and fifth push/pull cables being secured to the second pusher member, wherein retraction of the fourth and fifth bush/pull cables effects advancement of the second pusher member.

4. The adapter assembly of claim 2, wherein each of the second and third push/pull cables are secured to the first pair of guide members and the fourth and fifth push/pull cables are secured to a second pair of guide members.

5. The adapter assembly of claim 4, wherein the inner housing is cylindrical, each guide member of the first and second pairs of guide members is secured relative to the inner housing.

6. The adapter assembly of claim 2, wherein each of the first, second, and third drive assemblies include a transmission for converting high speed, low torque input to low speed, high torque output.

7. The adapter assembly of claim 2, wherein the coupling assembly connects each of the first, second, and third drive assemblies with respective first, second, and third drive shafts of a handle assembly.

8. The adapter assembly of claim 2, wherein the third drive assembly includes a third carriage assembly, the fourth and fifth push/pull cables being secured to the third carriage assembly.

9. The adapter assembly of claim 1, further comprising a trocar member, wherein the first push/pull cable is secured to the trocar member.

10. The adapter assembly of claim 1, wherein the first drive assembly includes a first carriage assembly and the second drive assembly includes a second carriage assembly, the first push/pull cable being secured to the first carriage assembly and the second and third push/pull cables being secured to the second carriage assembly.

11. The adapter assembly of claim 1, further including a trocar assembly, wherein the trocar assembly includes a locking member and a releasable trocar member.

12. The adapter assembly of claim 11, wherein the releasable trocar member is configured for operable engagement with an anvil assembly.

13. An adapter assembly operably connecting an end effector to a surgical stapling instrument, the adapter assembly comprising:
   a drive coupling assembly;
   a first drive assembly operably connected to the drive coupling assembly, the first drive assembly including a first push/pull cable;
   a second drive assembly operably connected to the drive coupling assembly, the second drive assembly including at least second and third push/pull cables; and
   an actuation assembly including a first pusher member and an inner housing,
   wherein the first pusher member is movably supported within the inner housing;
   wherein each of the second and third push/pull cables is secured relative to the inner housing by a first pair of guide members;
   wherein the second and third push/pull cables each include an outer sheath, a proximal end of each outer sheath being secured to a frame member of a proximal portion of the adapter assembly, the second and third push/pull cables and their corresponding outer sheaths each including a service slack,
   wherein the outer sheaths of the respective second and third push/pull cables engage the first pusher member, whereby retraction of the second and third push/pull cables reduces the service slack to advance the sheaths to cause distal movement of the first pusher member.

14. The adapter assembly of claim 13, further comprising a trocar member, wherein the first push/pull cable is secured to the trocar member.

15. The adapter assembly of claim 13, wherein the inner housing is cylindrical, each guide member of the first pair of guide members is secured relative to the inner housing.

16. The adapter assembly of claim 13, wherein at least one of the first and second assemblies include a transmission for converting high speed, low torque input to low speed, high torque output.

17. The adapter assembly of claim 13, further including a trocar assembly, wherein the trocar assembly includes a locking member and a releasable trocar member.

18. The adapter assembly of claim 17, wherein the releasable trocar member is configured for operable engagement with an anvil assembly.

19. The adapter assembly of claim 13, wherein the coupling assembly connects each of the first and second drive assemblies with respective first and second drive shafts of a handle assembly.

* * * * *